United States Patent
Goetz et al.

(10) Patent No.: US 9,238,135 B2
(45) Date of Patent: Jan. 19, 2016

(54) FLAGGING OF ELECTRODES OF AN IMPLANTABLE MEDICAL DEVICE, CONTROLLER, SYSTEM AND METHOD THEREFORE

(75) Inventors: Steven M. Goetz, Brooklyn Center, MN (US); Todd V. Smith, Shoreview, MN (US); Nathan A. Torgerson, Andover, MN (US); Warren W. Ball, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1234 days.

(21) Appl. No.: 12/112,612

(22) Filed: Apr. 30, 2008

(65) Prior Publication Data

US 2009/0276010 A1   Nov. 5, 2009

(51) Int. Cl.
*A61N 1/36* (2006.01)
*A61N 1/08* (2006.01)

(52) U.S. Cl.
CPC .............. *A61N 1/08* (2013.01); *A61N 1/36071* (2013.01); *A61N 1/36185* (2013.01)

(58) Field of Classification Search
CPC ........................ A61N 1/36128; A61N 1/36185
USPC ........................................................ 607/28
See application file for complete search history.

(56) References Cited

U.S. PATENT DOCUMENTS

| | | | |
|---|---|---|---|
| 4,719,922 A * | 1/1988 | Padjen et al. | 607/62 |
| 4,870,341 A | 9/1989 | Pihl et al. | |
| 5,487,755 A | 1/1996 | Snell et al. | |
| 5,549,654 A | 8/1996 | Powell | |
| 5,713,937 A | 2/1998 | Nappholz et al. | |
| 5,724,985 A | 3/1998 | Snell et al. | |
| 5,891,179 A | 4/1999 | Er et al. | |
| 6,101,415 A | 8/2000 | Er et al. | |
| 6,308,100 B1 | 10/2001 | Er et al. | |
| 6,374,139 B1 | 4/2002 | Er et al. | |
| 6,721,600 B2 | 4/2004 | Jorgenson et al. | |

(Continued)

FOREIGN PATENT DOCUMENTS

| WO | WO 9819738 A1 | 5/1998 |
|---|---|---|
| WO | WO 0143821 A1 | 6/2001 |

(Continued)

OTHER PUBLICATIONS

International Search Report for PCT/US2009/030980.

(Continued)

*Primary Examiner* — Eric D. Bertram
(74) *Attorney, Agent, or Firm* — IPLM Group, P.A.

(57) ABSTRACT

Method, controller and system for an implantable medical device having a plurality of electrodes, the implantable medical device capable of delivering therapeutic stimulation to a patient, comprising a control module, a user interface operatively coupled to the control module, the user interface providing control of the control module by a medical professional or other user, and an electrode interface operatively coupled between the plurality of electrodes and the control module. The control module uses the electrode interface to obtain a plurality of measurements of impedance values for a plurality of selected pairs of individual ones of the plurality of electrodes. The control module flags electrodes using the plurality of measurements of impedance values of the selected pairs of individual ones of the plurality of electrodes comparative to a range, and the delivery of therapy on flagged electrodes is inhibited.

39 Claims, 7 Drawing Sheets

(56) References Cited

U.S. PATENT DOCUMENTS

| | | |
|---|---|---|
| 6,748,274 B2 | 6/2004 | Levine et al. |
| 6,842,644 B2 | 1/2005 | Anderson et al. |
| 2002/0077669 A1 | 6/2002 | Lindh et al. |
| 2002/0120307 A1 | 8/2002 | Jorgenson et al. |
| 2003/0088289 A1 | 5/2003 | Levine et al. |
| 2003/0114899 A1 | 6/2003 | Woods et al. |
| 2003/0176899 A1 | 9/2003 | Samuelsson et al. |
| 2003/0204226 A1 | 10/2003 | Acosta et al. |
| 2004/0073266 A1* | 4/2004 | Haefner et al. ............ 607/27 |
| 2004/0082980 A1 | 4/2004 | Mouine et al. |
| 2004/0098063 A1 | 5/2004 | Goetz |
| 2004/0143303 A1 | 7/2004 | Sieracki |
| 2004/0225337 A1 | 11/2004 | Housworth et al. |
| 2005/0010258 A1 | 1/2005 | Peterson et al. |
| 2005/0033385 A1 | 2/2005 | Peterson et al. |
| 2005/0107841 A1 | 5/2005 | Meadows et al. |
| 2006/0036186 A1 | 2/2006 | Goetz et al. |
| 2006/0241710 A1* | 10/2006 | Rueter ............ 607/28 |
| 2008/0027526 A1 | 1/2008 | Zarembo |
| 2008/0051847 A1* | 2/2008 | Kelly ............ 607/30 |

FOREIGN PATENT DOCUMENTS

| | | |
|---|---|---|
| WO | WO 02/09808 A1 | 2/2002 |
| WO | WO 03077992 A1 | 9/2003 |
| WO | WO 2005068017 A1 | 7/2005 |
| WO | WO 2006017277 A2 | 2/2006 |
| WO | WO 2007112061 A2 | 10/2007 |
| WO | WO 2007112061 A3 | 10/2007 |

OTHER PUBLICATIONS

European Office Action for EP 09739268.2 dated Oct. 17, 2013.

\* cited by examiner

Figure 8

FLAGGING OF ELECTRODES OF AN IMPLANTABLE MEDICAL DEVICE, CONTROLLER, SYSTEM AND METHOD THEREFORE

FIELD

The present invention relates generally to controllers, systems and methods for implantable medical devices and, more particularly, to such controllers, systems and methods for implantable medical devices having therapeutic electrical stimulation electrodes.

BACKGROUND

The medical device industry produces a wide variety of electronic devices for treating patient medical conditions. Depending upon medical condition, medical devices can be surgically implanted or connected externally to the patient receiving treatment. Medical professionals or other clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices designed to deliver therapeutic electrical stimulation include neurological stimulators, pacemakers and defibrillators.

Implantable medical devices configured to deliver therapeutic electrical stimulation commonly deliver therapy via electrodes positioned on one or more leads operatively connected to the implantable medical device. In some instances, the housing of the implantable medical device may also serve as an electrode or an electrode may be positioned on the housing of the implantable medical device. The electrode or electrodes are commonly positioned in the patient's body during the same surgical procedure in which the implantable medical device is implanted. Sometimes the electrode or electrodes are placed in a follow-up procedure.

The positioning of electrodes, and associated leads, is often an inexact procedure and may commonly be dependent on the particular physiologic characteristics of the patient. In addition, electrodes may commonly be positioned within the patient without the medical professional or user conducting the procedure being capable of actually seeing where the electrodes are positioned. Instead, external aides such as fluoroscopes and/or endoscopes may commonly be employed to inform the medical professional or other user as to an approximate location of the electrodes. Electrodes may also be placed by stereotactic head frame which allows placement of the lead without direct visualization. Further, the ideal target is often not known a priori and time constraints may not allow for perfect targeting in the operating room.

Due to the inherent uncertainty involved in the placement of electrodes for an implantable medical device, implantable medical devices and the external controllers that interface with the devices are commonly operable to perform a test on the leads and electrodes to verify that the leads and electrodes are functioning properly and are positioned correctly. A common test is to check the impedance between pairs of electrodes. During testing, an electrode can be driven with a signal having known electrical characteristics. The signal may be measured, e.g., on another electrode or electrodes, and the impedance computed between electrodes using known fundamental relationships. The measured impedance value can give a medical professional or other user information relating to whether the electrodes involved in the test are positioned correctly and operating properly.

An external controller, e.g., a physician programmer, is commonly utilized in lead impedance tests. Physician programmers can be similar in size and composition to a large laptop computer. The physician programmer provides a user interface via a display screen, and is manipulated by a medical professional via a variety of inputs, such as buttons and touchscreens. The physician programmer commonly communicates with the implantable medical device via inductive telemetry. In order to accomplish this, a coil, operatively coupled to the controller, typically by a wire, is placed over a coil operatively coupled to the electronics in the implantable medical device producing an alternating current in the coil operatively coupled to the controller, thereby establishing an inductive link over which data may be passed in either direction. Because physician programmers are typically not sterilized, the physician programmer itself is placed outside of the sterile field, only the coil and its housing is taken inside the sterile field, e.g., using a sterile bag.

For example, United States Patent Application Publication No. 2006/0036186, Goetz et al, Automatic Impedance Measurement of an Implantable Medical Device, discloses a method and controller for automating impedance measurements. An entry for each electrode pair is displayed on a user interface. Each electrode pair entry includes an identification of electrodes for an electrode pair, an associated value of impedance and a value of current that is measured between the electrodes of a pair.

In another example, U.S. Pat. No. 5,891,179, Er et al, Method and Apparatus for Monitoring and Displaying Lead Impedance in Real-Time for an Implantable Medical Device, discloses a method and controller for displaying real-time graphical representations of variable lead impedance. Impedance values are calculated using Ohm's law or other related equations. The calculated impedance values are then output to a graphic display for presentation in graphical form or are output to a graphic printer, or both.

In another example, United States Patent Application Publication No. 2003/0114899, Samuelsson et al, Programming System for Medical Devices, discloses a method and controller for displaying graphical representations of a quantity influenced by the operation of a medical device. Such quantities may include information derived from tests and diagnostics, such as an electrode impedance test.

In another example, United States Patent Application Publication No. 2005/0033385, Peterson et al, Implantable Medical Device Programming Apparatus Having a Graphical User Interface, discloses graphical displays of the operation of a medical device, such as a test of a device lead. Results are organized according to the anatomical position of the lead, i.e., whether the lead is an atrial or ventricular lead, allowing the clinician to efficiently assess the functionally of all lead data by virtue of its grouping into precise anatomical categories.

In another example, U.S. Pat. No. 6,721,600, Jorgenson et al, Implantable Lead Functional Status Monitor and Method, discloses a system for obtaining trend data on the status of leads of an implantable medical device. The lead status measurement derives its data from various sources including lead impedance, non-physiologic sensed events, percentage of time the device is in mode switch, the results of capture management operation, sensed events, reversion paced counts, and refractory sense counts. The lead status measurement employs a set of weighted sum rules used by algorithms to process data from all of the above-mentioned sources to arrive at easily interpreted messages accessible to clinicians via an external programmer. Data from these sources identify lead conductor/connector interface issues and electrode/tissue interface issues indicative of lead-related mechanisms suggestive of impending or actual lead failure. The weights are "interpreted" for the user in the following manner either by indicating (1) lead-related parameters are all within range or operating normally; (2) one or more of the lead parameters are out-of-range and, thus, leads should be investigated; or (3) a number of lead parameters are out-of-range and a safety problem exists.

Messages to the user refer to three types of lead-related conditions: either lead/conductor/connector messages, lead insulation messages or biological interface messages. Examples of such messages include: (1) high impedance (>4000 ohms, 2× increase over reference, among others); (2) increase in threshold(s) above preset or programmed limit; and (3) reduction in R-wave and P-wave amplitude below preset or programmed limits.

Summary information from a variety of trend data is therefore presented for the use of a medical professional.

SUMMARY

But none of the above documents show, disclose or suggest the physician programmer taking any automatic actions in response to an electrode integrity metric, such as an impedance measurement. The physician programmer may prevent or inhibit any attempt by a medial professional to program or utilize a non-functional or suspect electrode, thereby potentially preventing harm to the patient in the event the medical professional willfully or accidentally ignores or disregards the results. Like much of the above cited documents, the controller provides a range of impedance values considered normal, bounded on either end by values fixed, e.g., set by the user or learned from previous tests or adaptively determined from other values in the current test, for the test.

In an embodiment, there is a controller for an implantable medical device having a plurality of electrodes. The implantable medical device is capable of delivering therapeutic stimulation to a patient using at least one of the plurality of electrodes. The controller has a control module, and an electrode interface operatively coupled between the plurality of electrodes and the control module. The control module uses the electrode interface to obtain a plurality of measurements of an integrity metric, such as an impedance value, for a plurality of selected sets of individual ones of the plurality of electrodes, and flags an individual one of the plurality of electrodes based on the plurality of measurements.

In an embodiment, a subset of the plurality of electrodes is flagged.

In an embodiment, the flagging is an indication of functionality of the individual one of the plurality of electrodes.

In an embodiment, the flagging is a binary indication of functionality of the individual one of the plurality of electrodes.

In an embodiment, the control module captures meta data related to the flagging of one of the plurality of electrodes.

In an embodiment, the meta data is an indication related to when flagging of one of the plurality of electrodes occurred.

In an embodiment, the control module inhibits delivery of the therapeutic stimulation on the individual one of the plurality of electrodes that is flagged.

In an embodiment, the control module automatically inhibits delivery of the therapeutic stimulation on the flagged individual one of the plurality of electrodes.

In an embodiment, the controller further comprises a user interface operatively coupled to the control module, the user interface providing control of the control module by a user.

In an embodiment, the user interface notifying the user if a flagged electrode only if existing therapeutic settings include settings that use the flagged electrode.

In an embodiment, the delivery of the automatically inhibited therapeutic stimulation may be overridden by the user via the user interface.

In an embodiment, the delivery of the automatically inhibited therapeutic stimulation may be overridden by the user via the user interface after a second measurement of impedance values for a plurality of selected sets of individual ones of the plurality of electrodes has been obtained.

In an embodiment, the flagging is based on an analysis of operational functionality of the plurality of electrodes using the plurality of measurements of impedance values of the selected sets of individual ones of the plurality of electrodes.

In an embodiment, flagging of one of the plurality of electrodes is based upon a manual input by user instead of or in addition to being based upon a plurality of measurements.

In an embodiment, there is a system for delivering therapeutic stimulation to a patient having an implantable medical device having a plurality of electrodes, and a controller.

The controller includes a control module and an electrode interface. The electrode interface is operatively coupled between the plurality of electrodes and the control module. The control module uses the electrode interface to obtain a plurality of measurements of an integrity metric, such as an impedance value, for a plurality of selected sets of individual ones of the plurality of electrodes, and flags an individual one of the plurality of electrodes based on the plurality of measurements.

In an embodiment, there is a method for delivering therapeutic stimulation to a patient using an implantable medical device having a plurality of electrodes. First, a plurality of measurements of an integrity metric, such as an impedance value, for a plurality of selected sets of individual ones of the plurality of electrodes is obtained. Then an individual one of the plurality of electrodes is flagged based on the plurality of measurements.

In an embodiment, the flagging step flags a subset of the plurality of electrodes.

In an embodiment, the flagging step flags the individual one of the plurality of electrodes based on functionality of the individual electrode.

In an embodiment, the flag is a binary flag.

In an embodiment, the flagging step captures meta data related to the flagging of one of the plurality of electrodes.

In an embodiment, the meta data is an indication related to when the flagging occurred.

In an embodiment, the method additionally has the step of inhibiting delivery of the therapeutic stimulation on the individual one of the plurality of electrodes that is flagged.

In an embodiment, the method additionally has the step of automatically inhibiting delivery of the therapeutic stimulation on the individual one of the plurality of electrodes that is flagged.

In an embodiment, the method additionally has the step of a user overriding the automatically inhibited delivery of the therapeutic stimulation.

In an embodiment, the method additionally has the step of a user overriding the automatically inhibited delivery of the therapeutic stimulation after a second measurement of impedance values for a plurality of selected sets of individual ones of the plurality of electrodes has been obtained.

In an embodiment, the method additionally has the step of analyzing the plurality of measurements of impedance values of the selected sets of individual ones of the plurality of electrodes, and wherein the flagging is based on the analysis.

In an embodiment, the flagging step flags an electrode based upon manual input by a user instead of or in addition to being based upon an integrity metric.

DESCRIPTION

Figure 1:
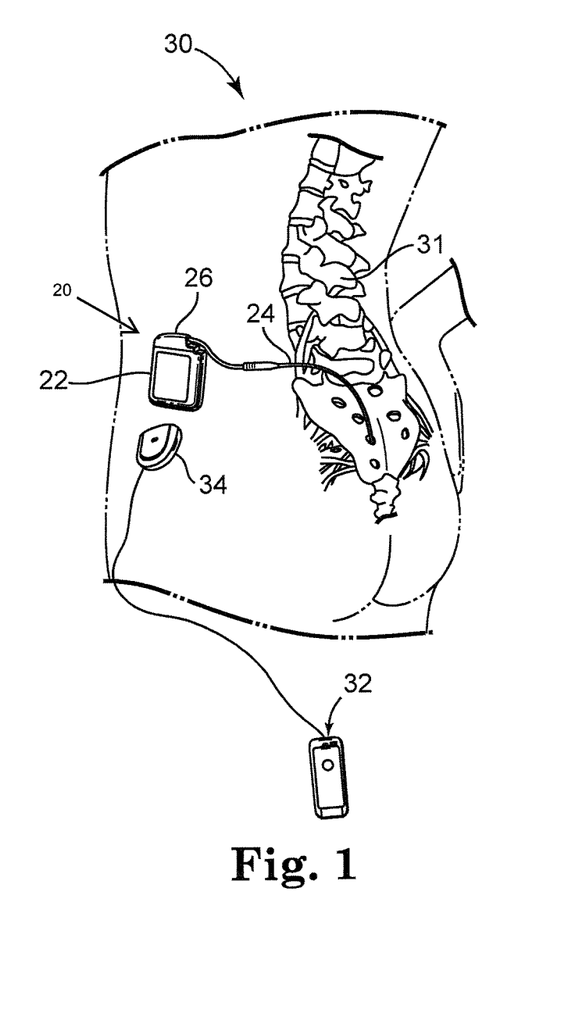
FIG. 1 shows an example of an implantable neurological stimulator implanted in the side of a patient, with electrodes positioned along the patient's sacral nerves.

FIG. 1 shows the general environment of one rechargeable implantable medical device 20 embodiment. Implantable neurological stimulator 22 is shown, but other embodiments such as pacemakers and defibrillators and the like are also applicable. Implantable neurological stimulator 22 is implanted subcutaneously in side 28 of patient 30. Lead 24 is operatively coupled to implantable neurological stimulator 22 at header 26. Lead 24 is positioned along spinal chord 31 of patient 30. Controller 32, which may be a physician programmer or patient programmer or another device, may become transcutaneously coupled to implantable neurological stimulator 22 via an inductive communication link through the tissue of patient 30 when controller 32 is placed in proximity to implantable neurological stimulator 22.

Figure 2:
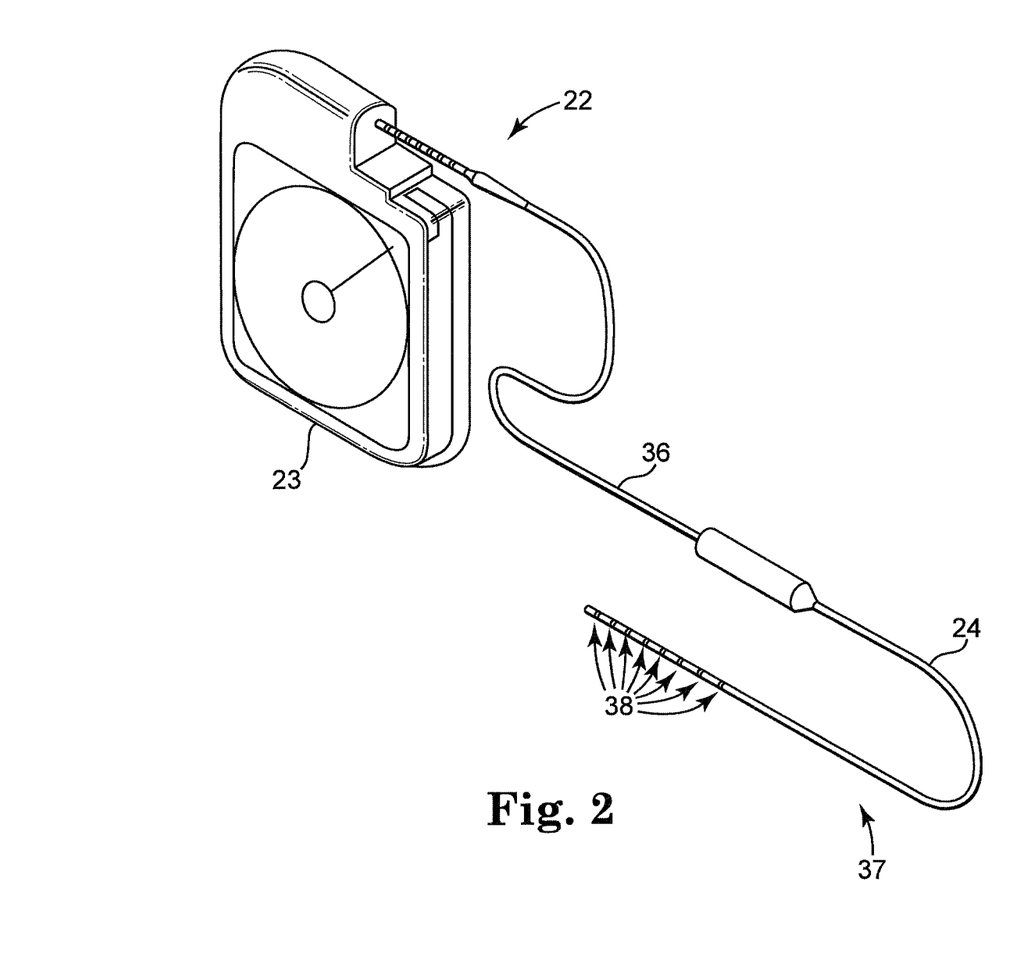
FIG. 2 shows an implantable neurological stimulator with a lead and lead extender and electrodes.
Figure 3:
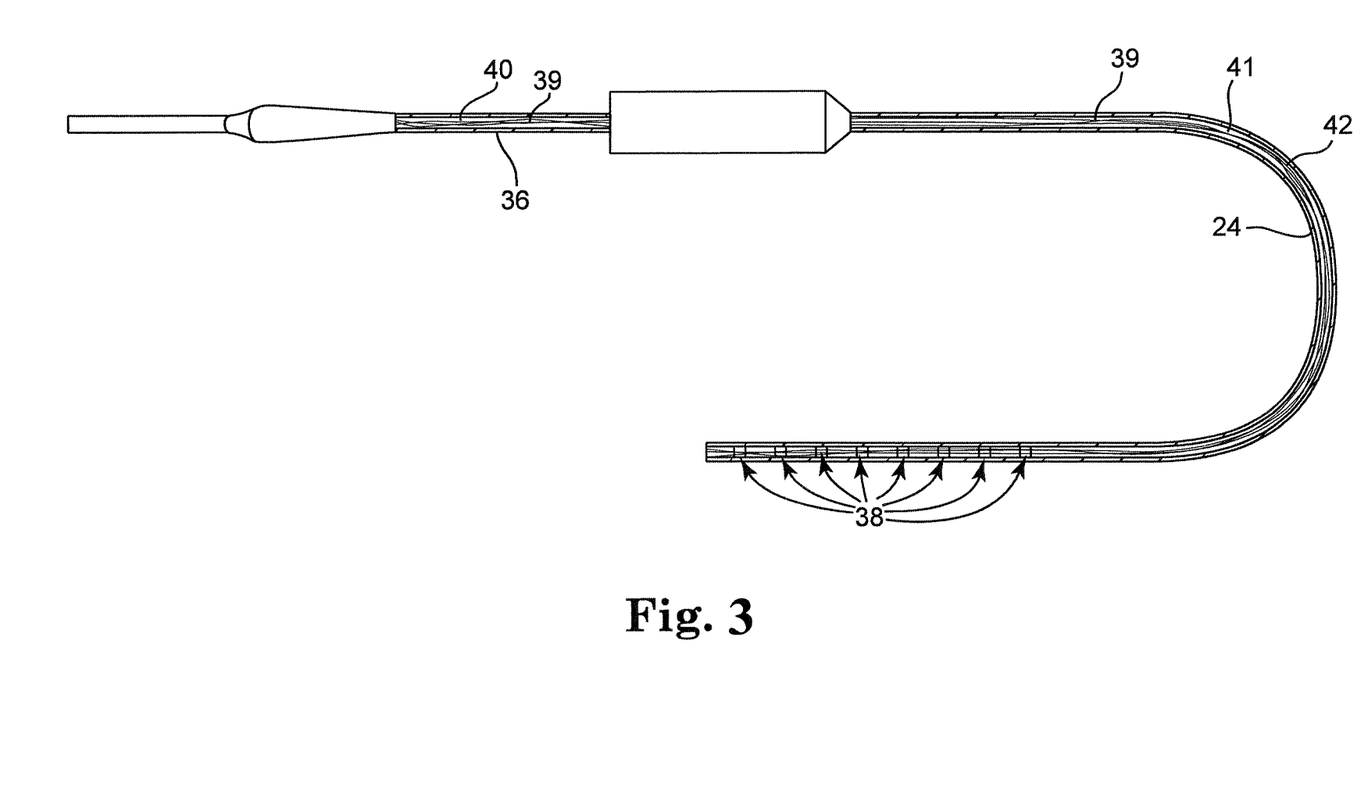
FIG. 3 shows a cutaway diagram of a lead with electrodes, and a lead extender, for an implantable medical device.

FIGS. 2 and 3 show a closer view of implantable neurological stimulator 22 and lead 24, operatively coupled by extender 36. Electrodes 38 are mounted on distal end 37 of lead 24. Electrodes 38 are comprised of a conductive material, in an embodiment, metal, that come into direct contact with tissue of patient 30. Electrodes 38 are operatively coupled with implantable neurological stimulator 22 via header 26 through wires 39 comprised of conductive material that pass through the interior 41 of lead 24 and are operatively coupled with conductive wires 39 in the interior 40 of extender 36. Insulation 42 is provided between wires 39 of lead 24.

Figure 4:
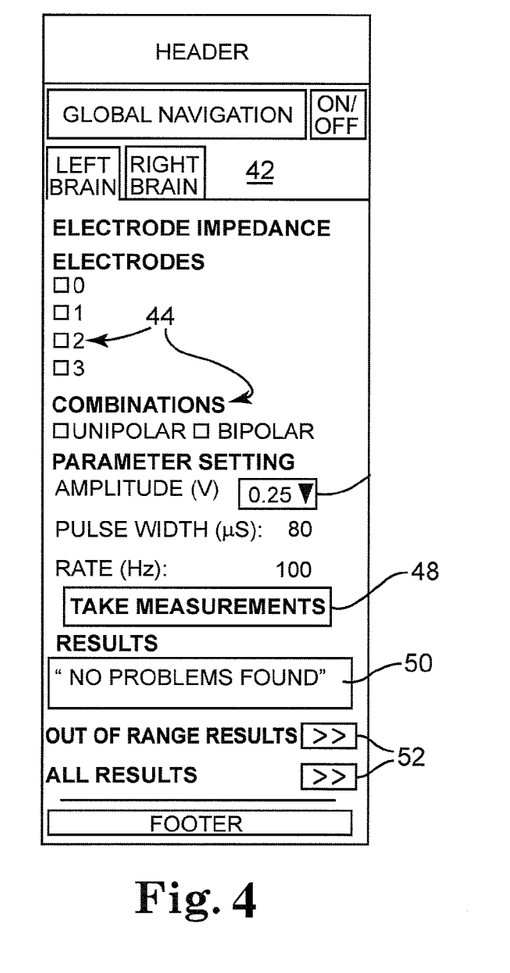
FIG. 4 shows a screen shot of a window for controlling an electrode impedance test of an implantable neurological stimulator.

FIG. 4 shows electrode impedance panel 42 for neurological stimulator 22, in this case a deep brain stimulator. Pick menus 44 allow selection of different leads 24 to test. Pressing button 48 begins the test according to default parameters. Alternatively, the test may begin without the necessity of a button press. After the test has completed a summary of the results is displayed in window 50, while buttons 52 give the medical professional or other user access to panel 60 (FIG. 5) that displays all results that were out of the predetermined range and to panel 80 (FIG. 6) that displays all results.

In a typical electrode impedance test, each electrode 38 may be tested both in unipolar mode and bipolar mode. Each electrode 38 in unipolar mode is paired up with neurological stimulator case 23 and the impedance between each electrode 38 and implantable neurological stimulator case 23 is measured and stored. In addition, each electrode 38 in bipolar mode is paired up with every other electrode 38 and the impedance between each electrode 38 and every other electrode 38 is measured and stored. An exception may be that electrodes 38 that are located in different physiologic regions of the body, e.g., the head, the chest, are never paired and tested.

While the electrode tests have been illustrated and described as being electrode impedance tests, it is to be recognized and understood that other forms of electrode integrity testing is also contemplated. In general, an integrity metric, which may be an impedance measurement, may be measured for a plurality of electrodes and the efficacy of each of the plurality of electrodes determined, at least in part. While electrode impedance is one such integrity metric, others are contemplated such as admittance, real or complex. Other integrity metrics could be the current into or out of a particular electrode or group of electrodes, voltage potential measured at an electrode due to stimulus on another electrode or electrodes, capacitance of an electrode with respect to another electrode or electrodes, inductance of an electrode with respect to another electrode or electrodes, frequency response of an electrode with respect to stimulus on another electrode or electrodes, measured reflection of a stimulus signal driven into an electrode (as in an electromagnetic transmission line).

Figure 5:
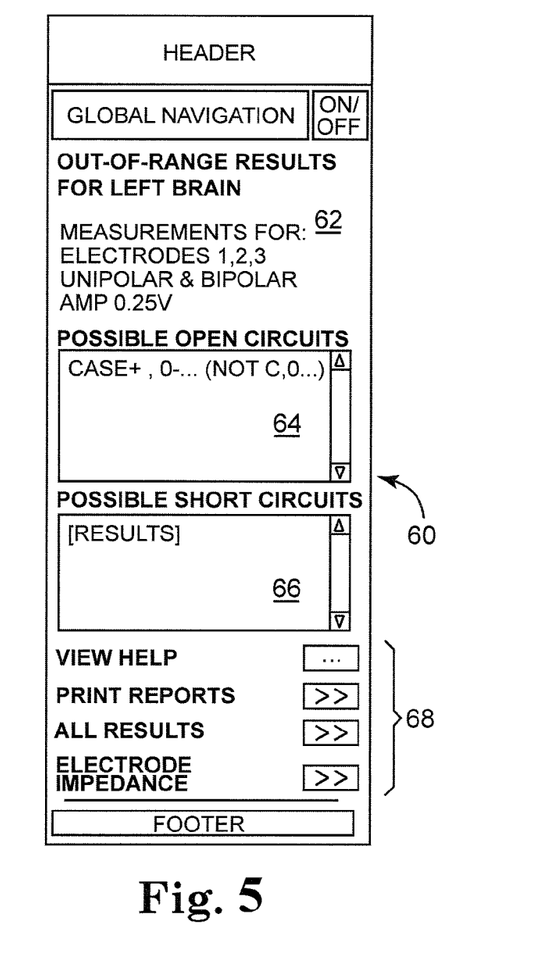
FIG. 5 shows a screen shot of a window for displaying out-of-range results of an electrode impedance test of an implantable neurological stimulator.

FIG. 5 shows out-of-range results panel 60 for displaying the results of testing initiated from electrode impedance panel 40. Text 62 at top of out-of-range results panel 60 informs the medical professional or other user what test the current results pertain to by displaying which electrodes 38 were tested, in which mode electrodes 38 were tested and at which voltage amplitude electrodes 38 were tested. Possible open circuits window 64 lists possible locations, e.g., all possible locations, of open circuits that cause faults of tested electrodes 38. Possible short circuits window 66 lists possible locations, e.g., all possible locations, of short circuits that cause faults. Buttons 68 provide access to out-of-range help panel 100 (FIG. 6a), all results panel 80 (FIG. 6b) and electrode impedance panel 40, as well as a print command to print the data displayed on out-of-range results panel 60. In an embodiment, results of electrode impedance tests are analyzed for selected sets of individual electrodes to determine operational functionality.

Open circuits are typically detectable when all measured impedance values for one electrode 38 are higher than the allowable maximum value. As an example, assume that electrodes 38 include six electrodes designated "electrode one", "electrode two", and so on through "electrode six". If all impedance values involving electrode two exceed the maximum value and all impedance values not involving electrode two are within the allowable value, the controller could conclude that an open circuit existed on the path along which electrode two was operatively coupled with implantable neurological stimulator 22. Similarly, if all measured impedance values pertaining to electrodes (38) two and six exceeded the maximum value and all impedance values not involving electrodes 38 two and six are within the allowable values, the controller could conclude that both electrodes two and six were open.

By contrast, short circuits are typically detectable when all measured impedance values involving those two electrodes 38 are lower than average and the measured impedance valve between the two electrodes 38 is below the minimum allowable value. For instance, if the average impedance between electrodes 38 is five hundred ohms, but between electrodes four and five, and four and six, in bipolar mode, and electrodes five and case 23 and six and case 23 were all four hundred ohms, and the impedance between electrodes five and six was below the allowable minimum value, controller 32 (FIG. 1) could conclude that there is a short circuit between electrodes five and six. Such short circuits can occur, among other reasons, because the electrodes 38 in question are physically touching, or insulation 42 between wires 39 operatively coupling electrodes 38 with implantable neurological stimulator 22 have frayed. Other examples of possible electrodes shorts are crushing of the lead body causing conductive wires to contact each other or adjoining wires and fluid ingress to a connector, e.g., lead to lead extension, lead extension to implantable medical device, lead to implantable medical device, causing one or more of the electrodes to short.

Occasionally, the results of testing may provide ambiguous results. For instance, if the impedance between electrodes zero and two, three and two and between electrode two and case are all greater than the maximum allowable value, but the impedance between electrodes one and two is within the allowable range, then it might not be clear what is the underlying cause of the issue. In circumstances where it is at least likely that a given individual electrode 38 or electrode 38 pair is not fully functional, an internal flag may be set in controller 32 corresponding to that electrode 38 or electrode 38 pair. Such an internal flag on an ambiguous result might be used to trigger further measurements or more aggressive measurements. Also, therapy on suspicious electrodes might be discourage, rather than prevented, in certain situations such as situations where the controller manages therapy creation or therapy settings. For example, a guided or wizard technique might try suspicious electrodes later in sequence or last.

In an embodiment, fewer than all of the electrodes measured are flagged, i.e., a subset of all of the electrodes measured are flagged.

In general, flagging consists of setting an internal flag associated with one or more of the plurality of electrodes measured. The flag thus set can be subsequently utilized by the controller to perform or to inhibit the performance of certain activities, such as inhibiting the use of a flagged electrode or electrode pair. The flag may also be communicated to a user who may then independently determine the use of the flagged electrode or electrode pair. In an embodiment, the user may only be notified of flagged electrodes if such flagged electrodes are included in currently selected therapeutic settings.

Flagging may also involve the capture of meta data, i.e., data intrinsic to the electrode or electrode pair being flagged and/or intrinsic to the flagging operation. As an example, information related to when the electrode or electrode pair is flagged may be captured as meta data and subsequently used by the controller or communicated to the user. This information could be, for example, the date and/or time of day that the electrode or electrode pair was flagged or an indication of an elapsed time since the electrode or electrode was flagged. Other types of meta data are also contemplated such as the type of measurement used to discover the flag, e.g., impedance versus current, settings or parameters used to make the measurement or measurements, type of procedure, life cycle state of the implantable medical device in which flagging occurs, whether a flagging condition was reproducible across multiple or all measurements and the type of measurements, whether the flagged electrode had previously been flagged, whether the user opted to override the flag either currently or in the past and whether the flagged event impacted therapy, i.e., was the flagged electrode being used in therapy.

Figures 6A, 6B:
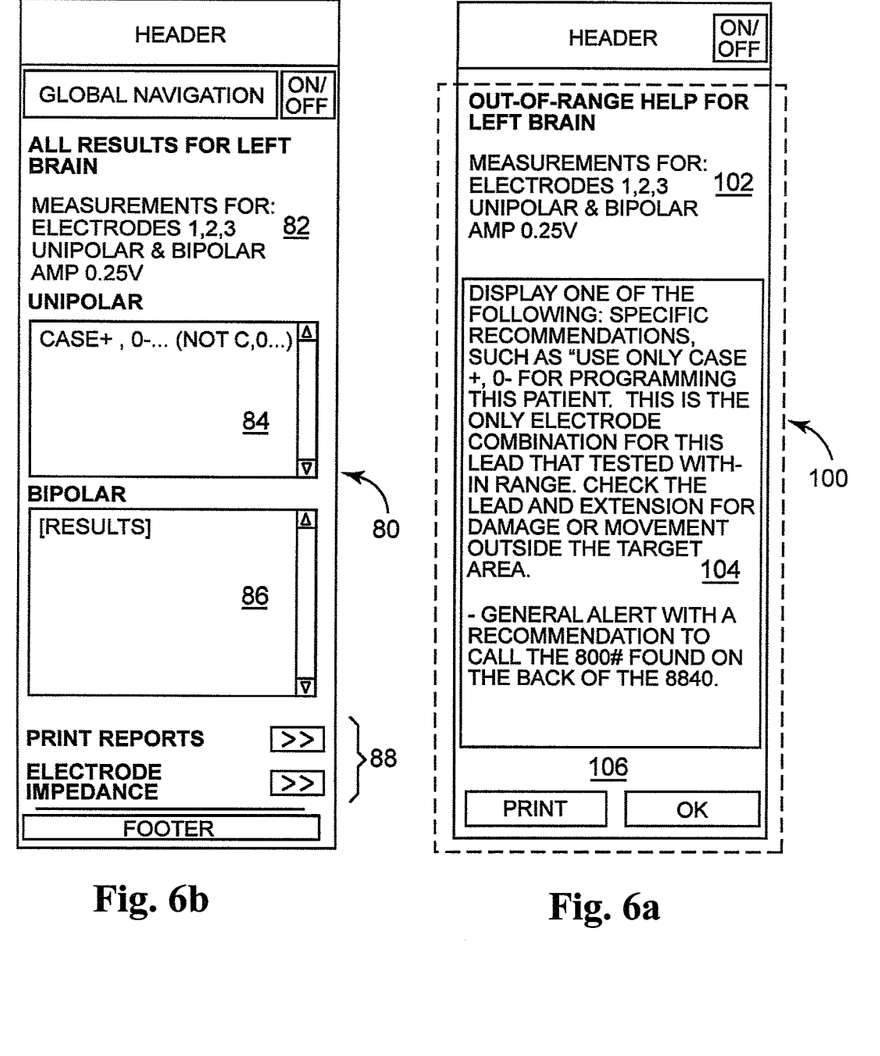
FIG. 6a shows a screen shot of an out-of-range help panel for an electrode impedance test of an implantable neurological stimulator.
FIG. 6b shows a screen shot of a window for displaying all results of an electrode impedance test of san implantable neurological stimulator.

FIG. 6 shows all results panel 80, for displaying all results of testing initiated from electrode impedance panel 40, regardless of whether testing resulted in an indication of failure or failures or not. Text 82 at the top of all results panel 80 informs the medical professional or other user to what test the current results pertain by displaying which electrodes 38 were tested, in which mode electrodes 38 were tested and at which voltage amplitude electrodes 38 were tested. Results are displayed in one of two windows 84, 86 depending on if the test mode was unipolar 84 or bipolar 86. Buttons 88 provide access to electrode impedance panel 40 and a print command.

Because an attempt to deliver therapy to patient 30 via a non-functional electrode 38 may cause undesirable consequences for the patient, including the possibility of injury and even death, controller 32 (FIG. 1) may prevent therapy from being delivered on flagged electrode 38 or electrode 38 pair. Where a clear conclusion can be drawn from the data, controller 32 may impose outright restrictions on the ability of a user to utilize a non-functional or suspect electrode 38. In the above example wherein electrodes five and six are shorted controller 120 may set an internal flag to prevent any programming of neurological stimulator 22 such that therapy is attempted to be delivered to patient 30 via electrodes five and six. Language may be appended to the result such as "Programming of electrodes five and six has been inhibited." In an embodiment, therapy on the suspect electrode 38 may not be permitted until a new test has been conducted and controller 32 determines that no further issues exist with any of the previously suspect electrodes 38. Note that in the above embodiment, where the internal flag has not been set then the electrode 38 pair may be taken to be functional and its use may not be automatically inhibited, thereby providing a binary indication of the functionality of the various electrodes 38.

Where a result is not considered sufficiently conclusive, or in situations where it is acceptable to allow a medical professional to override a determination of a suspect or non-functional electrode 38, controller may prompt the medical professional "Do you wish to override inhibiting electrodes five and six?".

In an embodiment of the above example, where the medical professional chooses to override, electrodes 38 five and six would once again be eligible to deliver therapy to patient 30. Where the medical professional gave a negative indication the inhibition may remain until either overridden by a medical professional, or a test indicating adequate functionality was run.

In an alternative embodiment, where a result is not considered sufficiently conclusive, or in situations where it is acceptable to allow a medical professional to override a determination of a suspect or non-functional electrode 38, controller may not automatically inhibit the programming of the suspect or non-functional electrodes 38, but rather prompt the medical professional whether or not to inhibit the suspect or non-functional electrodes. For instance, continuing with the above example, the medical professional may be prompted, "Do you want to inhibit therapy on electrodes 5 and 6?" Where the medical professional selects "no", the electrodes would not be inhibited. Where the medical professional selects "yes", the electrodes would be inhibited, in an embodiment until either a medical professional removes the inhibition, or a test is run that indicates electrodes 38 five and six are functioning properly. In an alternative embodiment, controller 120 may allow the medical professional to opt whether or not to inhibit, but may first require further testing, such as a full measurement test or a different type of measurement or a measurement made using different parameters, to provide as much information as possible prior to allowing the medical professional the option of inhibiting or not.

Figure 7:
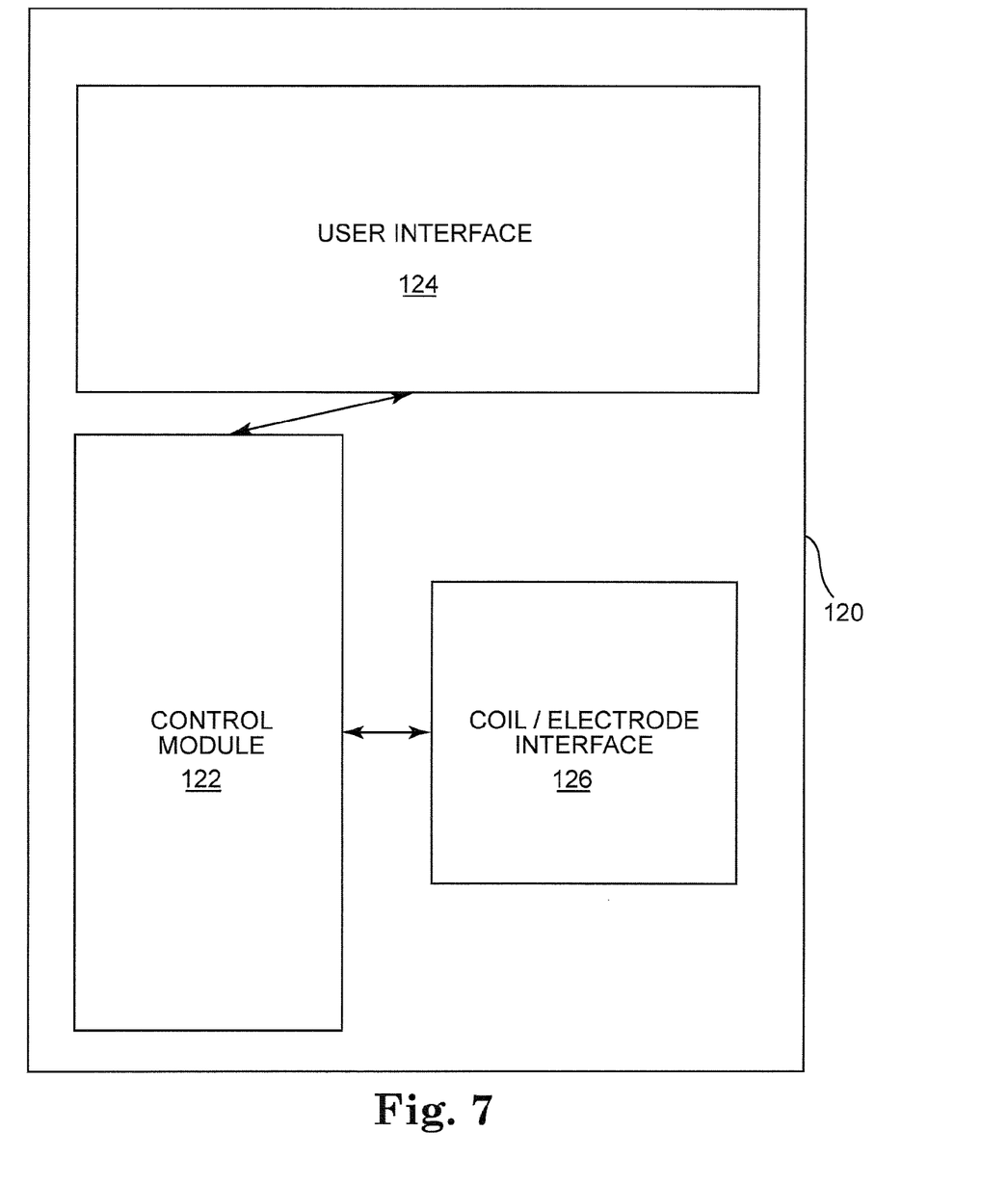
FIG. 7 shows a block diagram of a controller for an implantable medical device.

FIG. 7 shows a block diagram of the functional blocks of controller 32. Control module 122 comprises a variety of off the shelf electronic components commonly found in a variety of commercial applications, such as personal computers. These electronic components include: a microprocessor, RAM, ROM and hard disks. These off the shelf components are integrated into control module 122 and additional operational features are added via custom electronics. These custom electronics are comprised of off the shelf integrated circuits and discrete components, and programmable components, such as Field Programmable Gate Arrays (FPGAs), Digital Signal Processors (DSPs), custom integrated circuits and Printed Circuit Boards (PCBs). User interface 124 provides control of control module 122 by a user. User interface 124 is configured to perform functions related to the functions described with respect to FIGS. 4-6, such as overriding automatically inhibited therapeutic stimulation. Electrode interface 126 is operatively coupled between electrodes 38 and control module 122 and provides measurements of integrity metrics of electrodes 38 as described in detail above.

Figure 8:
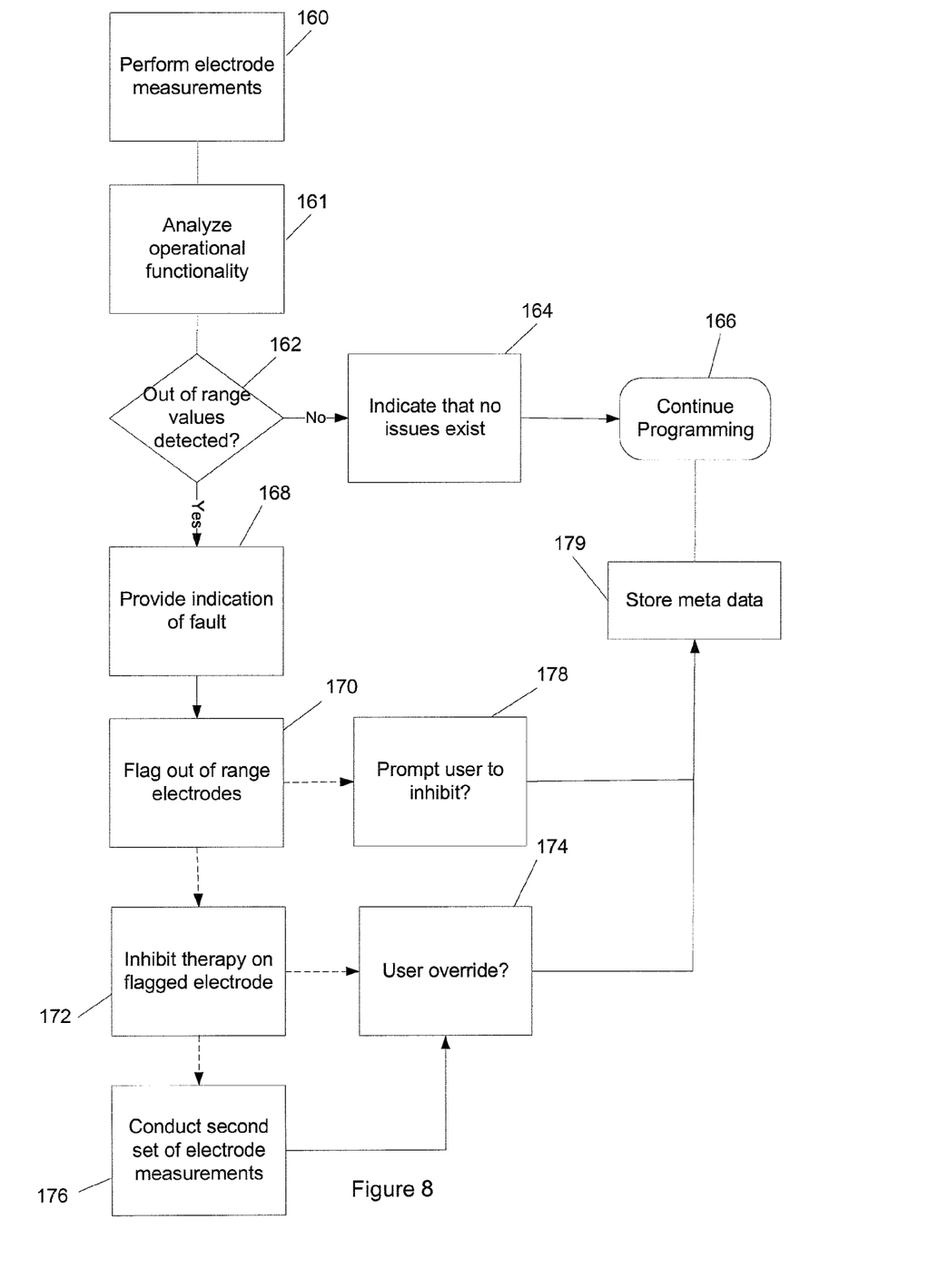
FIG. 8 is a flow chart for conducting an electrode impedance test for an implantable medical device.

FIG. 8 is a flow chart for conducting a standard electrode impedance test. In an embodiment, implantable neurological stimulator 22 performs an impedance measurement (160) involving minimal testing that still tests all electrode 38 pairs. In an alternative embodiment, impedance measurement (160) tests all electrodes 38 against all other electrodes 38, in which case each individual electrode 38 may be independently characterized. In an embodiment, an analysis is performed (161) of impedance measurements of electrodes 38 to determine operational functionality. In an embodiment, if all of the resulting measured impedance values are within (162) the allowable range controller 32 indicates that no issue exists (164) in results window 50 (FIG. 4), and the user may continue programming implantable neurological stimulator 22 (166) using controller 32.

In an embodiment, if any result is out of range, however, controller 32 indicates (168) the fault, and flags (170) the out-of-range electrodes 38. In embodiments in which impedance measurement (160) involves minimal testing, then electrode 38 pairs may be flagged (170) and indicated (168) to the user. In embodiments in which impedance measurement (160) involves characterizing electrodes 38 individually, individual electrodes 38 may be flagged (170). In an embodiment the user may specify that the impedance test may be repeated to verify the fault. While the results of electrode impedance tests may be compared against a fixed allowable range, an adaptive algorithm that compares all measured impedance values against the average of the measured impedance values is contemplated. Electrodes 38 or electrode 38 pairs that vary from the average may be flagged as suspect, deserving of further analysis.

In various embodiments, controller 32 may inhibit (172) delivery of therapeutic stimulation on electrodes 38 that have been flagged (170). In an embodiment, the inhibiting (172) is done automatically by controller 32. In an embodiment, the user may override (174) the inhibition placed (172) on electrode 38. In an alternative embodiment, the user may not be given the option of overriding (174). In an embodiment, controller 32 may require a second impedance measurement (176) of electrodes 38 before allowing the user to override (174). In alternative embodiments, the user may be prompted (178) whether to inhibit immediately after electrodes 38 are flagged (170). Optionally, meta data (as discussed above) may be stored (179). In either case, the user may continue programming implantable neurological stimulator 22 (166) using controller 32.

In an embodiment, an electrode or electrode pair, or any of the electrodes, may be flagged manually by a user, either instead of and/or in addition to the result of any measurement performed with respect to such electrode or electrode pair. For example, a medical professional may determine or suspect that a particular electrode or electrode pair may be providing non-advantageous results, such as unusual or abnormal behavior or intolerable side effects, and may manually flag such electrode or electrode pair to prevent, for example, the electrode or electrode pair to be subsequently utilized. This may be especially important because, in certain circumstances, the electrode or electrode may be technical functional, i.e., passing the integrity metric tests, such as impedance measurements, but still may be providing non-advantageous results. In an embodiment, testing by the controller, including prior, contemporaneous or subsequent testing, would not be allowed to remove the manually set flag. The reason an electrode or electrode has been manually flagged may be captured as meta data perhaps as well as the side effect caused or observed and the severity of such side effect.

Thus, embodiments of the controller for flagging suspect electrodes, system and method therefore are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A controller for an implantable medical device having a plurality of electrodes, said implantable medical device capable of delivering therapeutic stimulation to a patient using at least one of said plurality of electrodes, comprising:

a user interface configured to provide selection by a user from among said plurality of electrodes creating a selected set of electrodes;

a control module; and an electrode interface operatively coupled between said plurality of electrodes and said control module;

said control module using said electrode interface to obtain a plurality of measurements of an integrity metric for said plurality of electrodes in said selected set of electrodes;

said control module flagging an individual one of said plurality of electrodes in said selected set of electrodes based on said plurality of measurements;

wherein said controller captures meta data related to said flagging of said individual one of said plurality of electrodes;

wherein said control module is configured to automatically inhibit delivery of said therapeutic stimulation on said flagged individual one of said plurality of electrodes; and wherein said user interface is configured to provide control of said control module by a user and wherein inhibition of delivery of said therapeutic stimulation may be overridden by said user via said user interface.

2. The controller as in claim 1 wherein said integrity metric comprises at least one of impedance, voltage and current.

3. The controller as in claim 1 wherein said flagging is an indication of functionality of said individual one of said plurality of electrodes.

4. The controller as in claim 1 wherein said flagging is a binary indication of functionality of said individual one of said plurality of electrodes.

5. The controller as in claim 1 wherein said meta data comprises an indication related to when flagging of said individual one of said plurality of electrodes occurred.

6. The controller as in claim 1 wherein said control module is configured to inhibit delivery of said therapeutic stimulation on said individual one of said plurality of electrodes that is flagged.

7. The controller as in claim 1 wherein said inhibition of delivery of said therapeutic stimulation may be overridden by said user via said user interface after a second measurement of integrity metric for individual ones of said plurality of electrodes in said selected set of electrodes has been obtained.

8. The controller as in claim 1 wherein said flagging is based on an analysis of operational functionality of said plurality of electrodes using said plurality of measurements of said integrity metric of said selected set of electrodes.

9. The controller as in claim 1 wherein said meta data comprises a type of measurement used by said control module when said flagging of said individual one of said plurality of electrodes occurred.

10. The controller as in claim 1 wherein said meta data comprises parameters used to make said measurements for said individual one of said plurality of electrodes when said flagging occurred.

11. The controller as in claim 1 wherein said meta data comprises a life cycle state of said implantable medical device.

12. The controller as in claim 1 wherein said meta data comprises whether said individual one of said plurality of electrodes had been previously flagged.

13. A system for delivering therapeutic stimulation to a patient, comprising:
    an implantable medical device having a plurality of electrodes; and
    a controller, comprising:
        a user interface configured to provide selection by a user from among said plurality of electrodes creating a selected set of electrodes;
        a control module;
        an electrode interface operatively coupled between said plurality of electrodes and said control module;
        said control module using said electrode interface to obtain a plurality of measurements of an integrity metric for said plurality of electrodes in said selected set of electrodes; and
        said control module flagging an individual one of said plurality of electrodes in said selected set of electrodes based on said plurality of measurements;
        wherein said controller captures meta data related to said flagging of said individual one of said plurality of electrodes;
        wherein said control module is configured to automatically inhibit delivery of said therapeutic stimulation on said flagged individual one of said plurality of electrodes; and
        wherein said user interface is configured to provide control of said control module by a user and wherein inhibition of delivery of said therapeutic stimulation may be overridden by said user via said user interface.

14. The system as in claim 13 wherein said integrity metric comprises at least one of impedance, voltage and current.

15. The system as in claim 13 wherein said flagging is an indication of functionality of said individual one of said plurality of electrodes.

16. The system as in claim 13 wherein said flagging is a binary indication of functionality of said individual one of said plurality of electrodes.

17. The system as in claim 13 wherein said meta data comprises an indication related to when flagging of said individual one of said plurality of electrodes occurred.

18. The system as in claim 13 wherein said control module is configured to inhibit delivery of said therapeutic stimulation on said individual one of said plurality of electrodes that is flagged.

19. The system as in claim 13 wherein said inhibition of delivery of said therapeutic stimulation may be overridden by said user via said user interface after a second measurement of integrity metrics for individual ones of said plurality of electrodes in said selected set of electrodes has been obtained.

20. The system as in claim 13 wherein said flagging is based on an analysis of operational functionality of said plurality of electrodes using said plurality of measurements of integrity metrics of said selected set of electrodes.

21. The controller as in claim 13 wherein said meta data comprises whether said user has previously overridden said individual one of said plurality of electrodes had been previously flagged.

22. The controller as in claim 13 wherein said meta data comprises a type of measurement used by said control module when said flagging of said individual one of said plurality of electrodes occurred.

23. The controller as in claim 13 wherein said meta data comprises parameters used to make said measurements for said individual one of said plurality of electrodes when said flagging occurred.

24. The controller as in claim 13 wherein said meta data comprises a life cycle state of said implantable medical device.

25. The controller as in claim 13 wherein said meta data comprises whether said individual one of said plurality of electrodes had been previously flagged.

26. The controller as in claim 13 wherein said meta data comprises whether said user has previously overridden said individual one of said plurality of electrodes had been previously flagged.

27. A method for delivering therapeutic stimulation to a patient using an implantable medical device having a plurality of electrodes, comprising the steps of:
    selecting, by a user, from among said plurality of electrodes creating a selected set of electrodes;
    obtaining a plurality of measurements of an integrity metric for said plurality of electrodes in said selected set of electrodes;
    flagging an individual one of said plurality of electrodes in said selected set of electrodes based on said plurality of measurements;
    capturing meta data related to said flagging of an individual one of said plurality of electrodes;
    automatically inhibiting delivery of said therapeutic stimulation on said individual one of said plurality of electrodes that is flagged; and
    a user overriding said automatically inhibited delivery of said therapeutic stimulation.

28. The method as in claim 27 wherein said integrity metric comprises at least one of impedance, voltage and current.

29. The method as in claim 27 wherein said flagging step flags said individual one of said plurality of electrodes based on functionality of said individual electrode.

30. The method as in claim 29 wherein said flag is a binary flag.

31. The method as in claim 30 further comprising the step of inhibiting delivery of said therapeutic stimulation on said individual one of said plurality of electrodes that is flagged.

32. The method as in claim 27 wherein said meta data comprises an indication related to when flagging of said flagging of said individual one of said plurality of electrodes occurred.

33. The method as in claim 27 further comprising the step of a user overriding said automatically inhibited delivery of said therapeutic stimulation after a second measurement of integrity metrics for individual ones of said plurality of electrodes in said selected set of electrodes has been obtained.

34. The method as in claim 27 further comprising the step of analyzing said plurality of measurements of integrity metrics of said selected set of electrodes, and wherein said flagging is based on said analysis.

35. The controller as in claim 27 wherein said meta data comprises a type of measurement used by said control module when said flagging of said individual one of said plurality of electrodes occurred.

36. The controller as in claim 27 wherein said meta data comprises parameters used to make said measurements for said individual one of said plurality of electrodes when said flagging occurred.

37. The controller as in claim 27 wherein said meta data comprises a life cycle state of said implantable medical device.

38. The controller as in claim 27 wherein said meta data comprises whether said individual one of said plurality of electrodes had been previously flagged.

39. The controller as in claim 27 wherein said meta data comprises whether said user has previously overridden said individual one of said plurality of electrodes had been previously flagged.

* * * * *